United States Patent [19]

Mitsuhata et al.

[11] 4,368,144

[45] Jan. 11, 1983

[54] SILVER CATALYST FOR PRODUCTION OF ETHYLENE OXIDE

[75] Inventors: Masashi Mitsuhata, Yokohama; Fumio Watanabe, Kawasaki; Toshihiko Kumazawa, Yokohama, all of Japan

[73] Assignee: Nippon Shokubai Kagaku Kogyo Co., Ltd., Japan

[21] Appl. No.: 218,700

[22] Filed: Dec. 22, 1980

[51] Int. Cl.³ .................... B01J 21/04; B01J 23/04
[52] U.S. Cl. .................... 252/463; 549/534
[58] Field of Search .................... 252/463; 260/348.34

[56] References Cited

U.S. PATENT DOCUMENTS

| | | | |
|---|---|---|---|
| 3,201,199 | 8/1965 | Lindsay et al. | 252/463 X |
| 3,664,970 | 5/1972 | De Maio | 252/476 X |
| 3,957,834 | 5/1976 | Piccinini et al. | 252/476 X |
| 4,207,210 | 6/1980 | Kilty | 252/463 |
| 4,242,235 | 12/1980 | Cognion et al. | 252/463 X |

*Primary Examiner*—W. J. Shine
*Attorney, Agent, or Firm*—Omri M. Behr

[57] ABSTRACT

A silver catalyst for the production of ethylene oxide, comprising a granular α-alumina carrier having a sodium content of not more than 0.07% by weight and a specific surface area within the range of from 0.5 to 5 m²/g, a finely divided metallic silver deposited on said carrier in an amount within the range of from 5 to 25% by weight based on the total catalyst, and at least one member selected from the group consisting of alkali metals of Atomic Numbers 19 to 55 and alkali metal compounds said at least one member being in an amount within the range of from 0.001 to 0.05 gram equivalent weight per kilogram of the complete catalyst.

8 Claims, No Drawings

SILVER CATALYST FOR PRODUCTION OF ETHYLENE OXIDE

BACKGROUND OF THE INVENTION

1. Field of the Invention

This invention relates to a silver catalyst for the production of ethylene oxide. More particularly, this invention relates to a silver catalyst which is used in the production of ethylene oxide by the catalytic vapor phase oxidation of ethylene with molecular oxygen.

2. Description of Prior Arts

The catalyst which is used in the production, on a commercial scale, of ethylene oxide by the catalytic vapor phase oxidation of ethylene with molecular oxygen is required to possess high activity, high selectivity and high durability. Various studies have been made to date with a view to improving such properties of the catalyst. In this connection, efforts have been made to improve reaction promoters, carriers and silver compounds. Many reports covering reaction promoters are found in patents. For example, U.S. Pat. No. 3,962,136, U.S. Pat. No. 4,007,135, British Pat. No. 1,489,335, U.S. Pat. No. 4,039,561 disclose inventions relating to reaction promoters. Most of the inventions are directed to improving the properties of the catalyst by addition of alkali metals belonging in a limit confining within.

The existing carrier for the catalyst still leaves much to be clarified and improved. For example, physical properties of the carrier such as specific surface area, pore diameter, pore distribution, pore volume and porosity and chemical properties of such carrier materials as α-alumina, silicon, carbide, silica and zirconia await improvements for the sake of optimization.

It is, therefore, an object of this invention to provide a novel silver catalyst for the production of ethylene oxide.

Another object of this invention is to provide a silver catalyst of high activity, high selectivity and high durability for use in the production of ethylene oxide.

SUMMARY OF THE INVENTION

The objects described above are accomplished by a silver catalyst for the production of ethylene oxide, which silver catalyst comprises a granular α-alumina carrier having a sodium content of not more than 0.07% by weight and a specific surface area within the range of from 0.5 to 5 $m^2/g$, finely divided silver supported on the carrier in an amount within the range of from 5 to 25% by weight based on the total amount of the total catalyst, and at least one member selected from the group consisting of alkali metals of Atomic Numbers 19 to 55 and compounds of these alkali metals and supported on the carrier in an amount within the range of from 0.001 to 0.05 gram equivalent weight per kilogram of the total catalyst, said amount of the alkali metal or compound excluding the amount of the alkali metal or compound present naturally in the carrier.

Over past many years, we continued a research to seek carriers suitable for catalysts to be used in the production of ethylene oxide. The results of this research indicate that when an α-alumina carrier having a lower sodium content than the conventional carriers generally used on a commercial scale in the art is adopted, it can be used effectively in a form having a relatively large specific surface area generally refused adoption on a commercial scale in the art by reason of the poor selectivity exhibited by the complete catalyst incorporating such a carrier and further that particularly when this carrier is used in a catalyst incorporating an alkali metal and/or alkali metal compound as a reaction promoter, the produced catalyst enjoys high activity, high selectivity and high durability never attained by any of the conventional catalysts.

PREFERRED EMBODIMENT OF THE INVENTION

It is silver-based catalysts that are used in the production of ethylene oxide by the gas phase catalytic oxidation of ethylene with molecular oxygen. Quite naturally, most of them are carried catalysts in which catalysts are deposited on carriers. It is also widely known in the art that these carriers are invariably porous granular carriers formed preponderantly of alumina.

In spite of the simplicity of designation, the porous granular alumina carriers formed preponderantly of alumina come in a large variety of types. The physical properties of carriers such as specific surface area, pore distribution, pore volume, particle diameter and shape and the chemical properties of such ingredients of carriers as α-alumina, silica, silicon carbide and clay all very widely. These physical and chemical properties have great effects upon the performance of catalysts. Selection of a carrier possessing ideal performance for a catalyst of certain desired characteristics is an important task for those fully skilled in the art.

Of the various physical properties of carriers, the specific surface area demands close attention because it has some bearing upon the pore diameter and heavily affects the various performance of catalysts. From the standpoint of activity and durability, the specific surface area of a catalyst is better to be as large as possible and, in this connection, the carrier is desirable to possess as large a specific surface area as possible and, in this connection, the carrier is required to possess as large a specific surface area as permissible. To increase the specific surface area of a carrier, the alumina particles selected as the main ingredient of the carrier are required to possess as small a size as permissible. This fact inevitably implies that the pores formed in the carrier have a proportionally small size. The small size of pores is not advantageous from the standpoint of diffusion and retention of gas and removal of heat of reaction. It is also disadvantageous in respect that the exposed surface area of the carrier is proportionally large. All these factors lead to a decline in the selectivity of the catalyst. The statement that the specific surface area of the carrier is desired to be as large as possible, therefore, does not hold good at all times. The specific surface area has its own limit.

In most carriers heretofore adopted for catalysts used in commercial operations have specific surface area not exceeding 1 $m^2/g$, frequently even less than 0.5 $m^2/g$. There are area exceptions in which carriers having specific surface area exceeding 1 $m^2/g$ are used. The catalysts using such carriers, however, exhibit lower selectivity than the catalysts using carriers of smaller specific surface area.

We continued a study with a view to eliminating all these difficulties. Consequently, we have now found a method which, in spite of use of carrier having a specific surface area exceeding 0.5 $m^2/g$, produces a catalyst possessing improved rather than degraded selectivity and exhibiting enhanced rather than impaired activity and durability compared with the conventional catalyst.

To be brief, the improvement provided by this method is accomplished, namely by lowering the sodium content in the carrier. The decrease of the sodium content is particularly effective where the specific surface area of the carrier exceeds the level of 1 m²/g, and the effect of this decrease in the sodium content is especially conspicuous where the catalyst contains an alkali metal or an alkali metal compound in an increased amount. It is surprising to note that the various disadvantages issuing from the physical properties of the catalyst are improved by the chemical properties of the carrier, specifically the sodium content of the carrier. The values of the specific surface area indicated throughout this specification are those determined by the Brunauer-Emmett-Teller method (hereinafter referred to as BET method, for short).

It is ordinary that the α-alumina which is used in a carrier having a specific surface area of not more than 10 m²/g should contain a sodium component (chiefly in the form of $Na_2O$) in an amount of not less than 0.1% by weight (calculated as $Na_2O$) for a reason ascribable generally to the method of its preparation. It is consequently natural that the carrier formed of the α-alumina should contain a sodium component in an amount of not less than 0.1% by weight (calculated as $Na_2O$).

Almost all the carriers which have heretofore been used in the silver-based catalysts for the production of ethylene oxide are generally of the type described above. As regards the ingredients of such a carrier, it has been widely held that the α-alumina plays the role of a main ingredient. On the theory that the quality of the catalyst improves with the increasing α-alumina content, the practice of devoting efforts to producing carriers having α-alumina contents of more than 90% by weight has been established to a large extent. No appreciable attention has ever been paid to the other elements of the carrier. Much less, the sodium component which is apparently an extraneous existence in the carrier has received absolutely no attention.

According to our studies, it has been ascertained that the sodium component in the carrier has a delicate effect upon the quality of the catalyst. Particularly where the specific surface area of the carrier is kept below the level of 0.5 m²/g as is usually observed in the art, this undesirable effect dwindles in proportion as the specific surface area decreases. In contrast, where the specific surface area is increased over the level of 0.5 m²/g, this effect gradually increases with the increasing area and it finally becomes conspicuous as the area rises past 1 m²/g. This invention, however, permits use of a carrier which has a specific surface area greater than 1 m²/g and which has heretofore been refused adoption by reason of the adverse effect of such a large surface area upon the selectivity. Moreover, use of such a carrier even guarantees decided superiority in activity and selectivity to the produced catalyst.

As will be noted from the working examples cited afterward, when two given carriers have an equal specific surface area of about 1.5 m²/g and one of them is formed of α-alumina having a low sodium content of not more than 0.07% by weight and the other of α-alumina having a higher sodium content, the two catalysts produced by using these two carriers respectively and incorporating therein an alkali metal as prescribed produce an incredibly wide difference of more than 7% in selectivity, although this difference may be ascribable more or less to the other properties.

The question as to what mechanism brings about this notable improvement in the quality of catalyst still defies out comprehension. In the light of the fact that, despite the possibility of sodium being positively added as a reaction promoter in some if not all cases, the sodium content in the carrier is desired to be as low as possible, the fact that the difference of selectivity is about 4% where the two catalysts omit inclusion of the alkali metal and, further, the fact that heavy dependence upon pH of the adsorption of metallic ions such as onto alumina and silica is reported on literature, it may safely be inferred that the sodium component present in the carrier, during the impregnation of the carrier with a solution containing silver and an alkali metal, has some bearing upon the pH distribution in the carrier and strongly affects the elution and distribution of silver and, in particular, the alkali metal. It is believed that this pecular behavior of the sodium component has something to do with the quality of the catalyst. In this sense, the potassium component (mainly in the form of $K_2O$) present in the carrier is believed to have some bearing upon the catalyst quality. In our experiment, the effect aimed at by the present invention was amply obtained by simply decreasing the sodium component without changing the potassium content from the original level. The carrier contains potassium in the form of $K_2O$ in an amount of not less than 0.1% by weight from the beginning. It is possible that the effect of this invention will be further enhanced by lowering the potassium content of the carrier to below 0.07% by weight.

In order to make more effective use of the carrier having a specific surface area of not less than 0.5 m²/g and a low sodium content, therefore, it is essential that, as a reaction promoter, some other alkali metal or a compound thereof should be contained directly in the carrier or the metal silver layer or deposited on the surface of the metal silver layer.

The alkali metals and compounds thereof which are advantageously usable for this purpose are the alkali metals of Atomic Numbers 19 to 55, namely, potassium, rubidium and cesium, and their compounds. Cesium and cesium compounds are particularly effective among others enumerated above. Optionally, these alkali metals and their compounds may be used effectively in the form of a mixture of two or more members. At times, combined use of potassium and cesium proves to be more effective in improving activity, if not selectivity, than sole use of cesium.

Excess amounts of the alkali metals and or compounds thereof to the range described in known literatures are effective, and especially in case of using the carrier having large specific surface area, it should be discussed on over the conventional addition range.

The amount of the alkali metal and/or the alkali metal compound to be added in the production of the catalyst of the present invention is required to fall within the range of from 0.001 to 0.05 gram equivalent weight, incl., desirably from 0.001 to 0.035 gram equivalent weight, incl., per kilogram of the total catalyst. Preferably, this amount is greater than 0.008 gram equivalent weight and is not greater than 0.035 gram equivalent weight per kilogram of the total catalyst. The range specified above should be observed, no matter whether the alkali metals or the compounds thereof are used independently of one another or they are used in the form of a mixture of two or more members.

To the carrier to be used in this invention, all the conditions widely accepted in the art are applicable except that the specific surface area should fall within the range of from 0.5 to 5 m$^2$/g, and the sodium content should be not more than 0.07% by weight. Desirably, however, there may be used an α-alumina, carrier formed preponderantly of α-alumina, however, preferably in an amount of more than 90% by weight, which α-alumina carrier possesses an apparent porosity within the range of from 25 to 60%, a specific pore volume within the range of from 0.2 to 0.5 cc/g and a particle diameter within the range of from 3 to 20 mm. The specific surface area mentioned above falls more desirably within the range of from 1 to 5 m$^2$/g, preferably from 1 to 3 m$^2$/g. None of the carriers of satisfactory quality so far made available have a specific surface area exceeding 5 m$^2$/g. Carriers of such a large specific surface area, therefore, are impractical. The elements of the carrier other than the α-alumina and the sodium component (mainly in the form of $Na_2O$) are desired to be limited to the kinds and amounts normally found in the carriers generally used in the field.

The carrier to be used in the present invention is a refractory carrier composed of spheres, pellets, rings or particles of some other suitable shape. The particles of the carrier have an average equivalent diameter within the range of from 3 to 20 mm, preferably from 3 to 10 mm.

The silver content is required to fall within the range of from 5 to 25% by weight, preferably from 10 to 20% by weight, based on the total catalyst. Deposition of silver in an amount exceeding 25% by weight is meaningless and wasteful.

The catalyst of this invention can be produced by any of the methods heretofore known to the art. Generally, this production is accomplished by impregnating the aforementioned carrier with an aqueous solution or an organic solvent solution of a soluble silver salt such as, for example, aqueous silver nitrate solution, ammonia solution or organic amine solution of an inorganic or organic acid silver salt, or aqueous silver lactate solution. The alkali metal or alkali metal compound may be deposited in advance on the carrier, added simultaneously to the aforementioned silver solution or deposited on the carrier after deposition of the metal silver.

Subsequently, there is performed a step of heating the impregnated carrier thereby decomposing or reducing the decomposable components and giving rise to a complete catalyst or a step of reductively decomposing the impregnated carrier within a reducing condition thereby giving rise to a complete catalyst.

To be more specific, the present invention relates to a silver catalyst to be used in the production of ethylene oxide by the gas phase catalytic oxidation of ethylene with molecular oxygen, which silver catalyst is obtained by using, as a porous refractory carrier therefore, a carrier having a sodium content of not more than 0.07% by weight, a specific surface area within the range of from 0.5 to 5 m$^2$/g, preferably from 1 to 5 m$^2$/g, an apparent porosity within the range of from 25 to 60%, a specific pore volume within the range of from 0.2 to 0.5 cc/g, and a particle diameter within the range of from 3 to 20 mm, impregnating this carrier with a solution of decomposable silver such as an amine solution of a silver salt of an organic acid and thereafter heating the impregnated carrier at a temperature within the range of from 100° to 300° C. thereby causing reduction or thermal decomposition of silver. The silver is deposited on the inner and outer surface of the carrier in the form of a finely divided powder in an amount within the range of from 5 to 25% by weight, preferably from 10 to 20% by weight, based on the complete catalyst.

The alkali metal or alkali metal compound, which is at least one member selected from the group consisting of potassium, rubidium and cesium and compounds of these elements, is added in the form of an aqueous solution or alcoholic solution to the silver solution in an amount within the range of from 0.001 to 0.05 gram equivalent weight, desirably from 0.001 to 0.035 gram equivalent weight, and preferably in an amount greater than 0.008 gram equivalent weight and not greater than 0.035 gram equivalent weight, per kilogram of the total catalyst. The resultant mixed solution is applied to the carrier by the method described above so that the alkali metal or alkali metal compound is deposited, in a state dispersed in silver being simultaneously deposited, on the carrier. Alternatively, the aforementioned solution of the alkali metal or alkali metal compound is directly applied to the carrier so that the alkali metal or alkali metal compound is deposited on the carrier before silver is deposited. Otherwise, silver is first deposited on the carrier and subsequently the solution is applied to the carrier so that the alkali metal or alkali metal compound is deposited on the carrier which already has silver deposited thereon.

The resultant silver catalyst containing the alkali metal is finally activated in a current of air at 100° to 400° C. for 10 to 100 hours to give rise to a complete catalyst.

The conditions which can be adopted for the production of ethylene oxide by the oxidation of ethylene with molecular oxygen in the presence of the silver catalyst prepared by the method described above are those which have heretofore been invariably known in the art. The general conditions involved in the commercial production of ethylene oxide, namely a feed gas composition consisting of 0.5 to 40% by volume of ethylene, 3 to 10% by volume of oxygen, 5 to 30% by volume of carbon dioxide and the balance to make up 100% by volume of other compounds including an inert gas such as nitrogen, argon or steam, a lower hydrocarbon such as methane or ethane and a halide such as ethylene dichloride or diphenyl chloride which serves the part of a reaction inhibitor, a space velocity of the feed gas falling within the range of from 1,000 to 10,000 hr$^{-1}$ (S.T.P.) and a pressure within the range of from 2 to 40 kg/cm$^2$ can be advantageously adopted.

Now, the present invention will be described more specifically with reference to working examples and comparative experiments. The present invention, illustrated and not limited in any way of these working examples, may be allowed modifications and alterations without departing from the spirit thereof.

The numerical values of conversion and selectivity indicated in whole specification including the working examples and comparative experiments which follow have been calculated in accordance with the following formulas.

$$\text{Conversion (\%)} = \frac{\text{Moles of ethylene converted}}{\text{Moles of ethylene fed}} \times 100$$

$$\text{Selectivity (\%)} = \frac{\text{Moles of ethylene oxide formed}}{\text{Moles of ethylene converted}} \times 100$$

EXAMPLE 1

A slurry was prepared of 570 g of silver carbonate and 200 ml of water. In the slurry, 560 ml of ethanolamine was thoroughly dissolved by stirring. The resultant solution was thoroughly stirred with 500 ml of water, and then stirred with 10 ml of an aqueous solution of 18.5% by weight potassium nitrate and 10 ml of an aqueous solution of 36.0% by weight cesium nitrate, to prepare an impregnating solution. With this solution was impregnated, 4,000 ml of a preheated α-alumina carrier which had an apparent porosity of 51%, a BET specific surface area of 1.54 m$^2$/g, a pore volume of 0.34 cc/g, a particle diameter of 5 mm and a sodium content of not more than 0.05% by weight (calculated Na$_2$O). The solution containing the impregnated carrier was gently stirred and heated at 80° to 120° C. for 2 hours.

The catalyst thus obtained was packed in a reaction tube of stainless steel 25.0 mm in inside diameter and 11,000 mm in length. With the exterior of the tube gradually heated with a heat medium from 100° C. to 240° C., air was passed through the bed of catalyst within the tube at 240° C. for 24 hours to activate the catalyst with the hot air.

Then, the temperature of the heat medium was lowered to 180° C. and the current of air was stopped. Instead, a mixed gas consisting of 20% by volume of ethylene, 8% by volume of oxygen, 7% by volume of carbon dioxide and the balance to make up 100% by volume of inert gases such as nitrogen, methane, ethane and argon plus 1 ppm of ethylene dichloride was fed to the reaction tube under a reaction pressure of 24 kg/cm$^2$ G and a space velocity of 5,500 hr$^{-1}$ (S.T.P.) and the temperature of the heat medium was elevated to 233° C. to effect a reaction. The results were as shown in Table 1.

CONTROL 1

A catalyst was prepared by following the procedure of Example 1, except that an α-alumina carrier having an apparent proposity of 53%, a BET specific surface area of 1.51 m$^2$/g, a pore volume of 0.31 cc/g, a particle size of 5 mm and a sodium content of 0.40% by weight (calculated as Na$_2$O) was used in the place of the carrier of Example 1. Then, the reaction of ethylene was carried out by the procedure of Example 1, except that the reaction temperature (temperature of the heat medium) was changed to 240° C. The results were as shown in Table 1.

TABLE 1

| | Ingredients of carrier (% by weight) | | Specific surface area of carrier (m$^2$/g) | Silver content (% by weight) | Amount alkali compound added* (gram equivalent weight/ kg of catalyst) | Result of reaction | | |
|---|---|---|---|---|---|---|---|---|
| | Al$_2$O$_3$ | Na$_2$O | | | | Reaction temperature (°C.) | conversion (%) | selectivity (%) |
| Example 1 | 94.5 | not more than 0.05 | 1.54 | 10 | 8.35 × 10$^{-3}$ | 233 | 8 | 82.5 |
| Control 1 | 94.0 | 0.40 | 1.51 | 10 | 8.35 × 10$^{-3}$ | 240 | 8 | 75.1 |

*The amount of alkali metal compound added is the total of the amount of potassium compound and that of cesium compound.

CONTROL 2

Catalysts were prepared by following the procedures of Example 1 and Control 1, except that the addition of the alkali metal compound was omitted. The reactions were carried out by following the procedures of Example 1 and Control 1 respectively, except that the reaction temperatures were fixed at the values indicated in Table 2. The results were as shown in Table 2. (Note that Control 2 corresponds to Example 1 and Control 3 to Control respectively.)

TABLE 2

| | Specific surface area of carrier (m$^2$/g) | Silver content (% by weight) | Ingredients of carrier (% by weight) (Na$_2$O) | Results of 10 days' reaction | | |
|---|---|---|---|---|---|---|
| | | | | Reaction temperature (%) | Conversion (%) | Selectivity (%) |
| Control 2 | 1.54 | 10 | not more than 0.05 | 197 | 8 | 74.3 |
| Control 3 | 1.51 | 10 | 0.40 | 210 | 8 | 70.5 |

EXAMPLES 2 TO 4

Catalyst were prepared by following the procedure of Example 1, except for the conditions shown in Table 3. The reactions of ethylene were carried out under the conditions involved in Example 1.

The results were as shown in Table 3.

CONTROLS 4 AND 5

Catalysts were prepared by following the procedure of Example 1, except for the conditions shown in Table 3. The reactions of ethylene were carried out under the conditions involved in Example 1.

The results were as shown in Table 3.

TABLE 3

| | Ingredients of carrier (% by weight) | | Properties of carrier | | | Silver content (% by weight) | Amount of alkali compound added (gram equivalent weight/kg of catalyst) | | Results of reaction | | |
|---|---|---|---|---|---|---|---|---|---|---|---|
| | | | Specific surface area | Apparent porosity | Pore volume | | | | Reaction temperature | Conversion | Selectivity |
| | $Al_2O_3$ | $NaO_2$ | $(m^2/g)$ | (%) | (%) | | Compound | Amount | (°C.) | (%) | (%) |
| Example 2 | 95.1 | 0.07 | 0.68 | 54 | 0.32 | 10 | $CsNO_3$ | $3.05 \times 10^{-3}$ | 221 | 8 | 81.3 |
| Example 3 | 95.3 | 0.05 | 2.62 | 50 | 0.37 | 10 | $KNO_3$ | $2.18 \times 10^{-2}$ | 216 | 8 | 76.5 |
| Example 4 | 97.0 | 0.05 | 4.51 | 45 | 0.40 | 10 | $CsNO_3$ | $2.50 \times 10^{-2}$ | 209 | 8 | 79.1 |
| Control 4 | 96.5 | 0.36 | 2.03 | 51 | 0.30 | 10 | $NKO_3$ | $1.70 \times 10^{-2}$ | 241 | 8 | 70.3 |
| Control 5 | 97.3 | 0.53 | 4.83 | 47 | 0.31 | 10 | $CsNO_3$ | $2.70 \times 10^{-2}$ | 260 | combustion | — |

What is claimed is:

1. A silver catalyst for the production of ethylene oxide, comprising a granular α-alumina carrier having a sodium content of not more than 0.07% by weight and a specific surface area within the range of from 0.5 to 5 $m^2/g$, a finely divided metallic silver deposited on said carrier in an amount within the range of from 5 to 25% by weight based on the total catalyst, and at least one member selected from the group consisting of alkali metals of Atomic Numbers 19 to 55 and alkali metal compounds, said at least one member being in an amount within the range of from 0.001 to 0.05 gram equivalent weight per kilogram of the total catalyst.

2. A catalyst set forth in claim 1, wherein the at least one member selected from said alkali metals and alkali metal compounds is deposited on the carrier in an amount within the range of from 0.001 to 0.035 gram equivalent weight per kilogram of the total catalyst.

3. A catalyst set forth in claim 2, wherein the at least one member selected from said alkali metals and alkali metal compounds is deposited on the carrier in an amount more than 0.008 gram equivalent total weight and not greater than 0.035 gram equivalent weight per kilogram of the complete catalyst.

4. A silver catalyst set forth in claim 1, wherein the specific surface area of the carrier is within the range of from 1 to 5 $m^2/g$.

5. A silver catalyst set forth in claim 4, wherein the specific surface area of the carrier is within the range of from 1 to 3 $m^2/g$.

6. A silver catalyst set forth in claim 1, wherein the alkali metal is cesium.

7. A silver catalyst set forth in claim 6, wherein the at least one member selected from said alkali metals and compounds of alkali metals is deposited on the carrier in an amount greater than 0.008 gram equivalent weight and not greater than 0.035 gram equivalent weight per kilogram of the total catalyst.

8. A silver catalyst set forth in claim 1, wherein the at least one member selected from said alkali metals and alkali metal compounds is dispersed within the finely divided silver.

* * * * *